United States Patent

Suzukamo et al.

[11] Patent Number: 4,463,188
[45] Date of Patent: Jul. 31, 1984

[54] METHOD FOR RACEMIZATION OF OPTICALLY ACTIVE 2,2-DIMETHYLCYCLOPROPANE-1-CARBOXYLIC ACID

[75] Inventors: Gohfu Suzukamo, Osaka; Masami Fukao; Yukio Yoneyoshi, both of Shiga, all of Japan

[73] Assignee: Sumitomo Chemical Company, Limited, Osoda, Japan

[21] Appl. No.: 481,946

[30] Foreign Application Priority Data

Apr. 6, 1982 [JP] Japan .................................. 57-57488

[22] Filed: Apr. 4, 1983

[51] Int. Cl.³ ........................ C07C 51/58; C07C 51/04
[52] U.S. Cl. ................................. 562/506; 260/544 L
[58] Field of Search .............................. 562/506, 401; 260/544 L

[56] References Cited

U.S. PATENT DOCUMENTS 4,008,268  2/1977  Mizutani ............................ 562/506
4,182,906  1/1980  Suzukamo .......................... 562/401

FOREIGN PATENT DOCUMENTS 10573  5/1980  European Pat. Off. .
1260847  1/1972  United Kingdom .

Primary Examiner—Michael L. Shippen
Attorney, Agent, or Firm—Cushman, Darby & Cushman

[57] ABSTRACT

A method for racemization of optically active 2,2-dimethylcyclopropane-1-carboxylic acid by converting said acid to the corresponding halide thereof represented by the general formula;

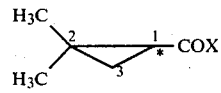

wherein X is a halogen atom, which is heated to a temperature of about 80° C. to about 300° C., preferably about 100° C. to about 200° C., and then, if desired, producing 2,2-dimethylcyclopropane-1-carboxylic acid by hydrolysis of the resultant acid halide.

5 Claims, No Drawings

METHOD FOR RACEMIZATION OF OPTICALLY ACTIVE 2,2-DIMETHYLCYCLOPROPANE-1-CARBOXYLIC ACID

This invention relates to a method for racemization of optically active 2,2-dimethylcyclopropane-1-carboxylic acid. More particularly, it relates to a method for racemization of optically active 2,2-dimethylcyclopropane-1-carboxylic acid, characterized by converting optically active 2,2-dimethylcyclopropane-1-carboxylic acid to a corresponding halide thereof represented by the general formula (I);

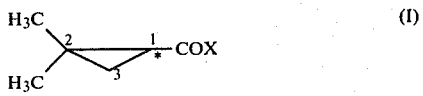

wherein X is a halogen atom, racemizing the said acid halide by heating it and then, if desired, hydrolyzing the resulting acid halide to produce 2,2-dimethylcyclopropane-1-carboxylic acid represented by the formula (II);

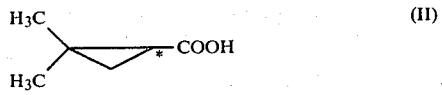

2,2-Dimethylcyclopropane-1-carboxylic acid is useful as intermediates for medicines and agricultural chemicals.

For example, said acid has been reported to be used as an intermediate of inhibitors for Dehydropeptidase-I [see "Kagaku to Seibutsu", 19, 204 (1981)].

Furthermore, esters of said acid with substituted furfuryl alcohols have been known to exhibit similar actions to those of esters called pyrethroid insecticides which are useful as rapid knock-down insectisides with low mammalian toxicity. (See British Pat. No. 1,260,847.)

Generally, one particular isomer of optically active isomers is often desired for such applications as medicines, agricultural chemicals, etc. Also, in the case of 2,2-dimethylcyclopropane-1-carboxylic acid to be objected in the present invention, use of one particular isomer of optically active isomers can attain more advantageous effects for such applications as mentioned above.

2,2-Dimethylcyclopropane-1-carboxylic acid is synthesized as racemic modification, namely ($\pm$) form by the usual method and an optically active form can be obtained by optical resolution of said racemic modification with optically active organic bases. [See Japanese Patent Kokai (Laid-open) No. 55-40669 and British Pat. No. 1,260,847.]

The racemized modification obtained by the method of the present invention can be subjected to the optical resolution. Accordingly, the method of the present invention for racemizing the residual enantiomer after optical resolution of one particular isomer, further in combination with a method of optical resolution of the thus obtained racemic modification, makes it possible to convert the acid into desired optically active form although the acid is initially in racemic form. Thus such an efficient method of racemization is industrially very significant.

Optically active 2,2-dimethylcyclopropane-1-carboxylic acid contains cyclopropane ring having high strain and it is difficult to racemize the acid without cleavage of the ring. Thus far there has been no knowing as to method for racemization of optically active 2,2-dimethylcyclopropane-1-carboxylic acid.

As the result of an extensive study, it has now been found that the racemization of the optically active 2,2-dimethylcyclopropane-1-carboxylic acid can be effected without cleavage of cyclopropane ring by once converting the acid to the corresponding halide thereof represented by the above general formula (I) which is then heated and then, if desired, hydrolyzing the resultant acid halide to produce 2,2-dimethylcyclopropane-1-carboxylic acid represented by the above formula (II). The present invention has been completed on the basis of the above finding.

Namely, first, the present invention provides a method for racemization of an optically active 2,2-dimethylcyclopropane-1-carboxylic acid halide which comprises heating an optically active 2,2-dimethylcyclopropane-1-carboxylic acid halide represented by the above general formula (I) to a temperature of about 80° C. to about 300° C.

Second, the present invention provides a method for racemization of optically active 2,2-dimethylcyclopropane-1-carboxylic acid which comprises converting optically active 2,2-dimethylcyclopropane-1-carboxylic acid to a corresponding halide thereof represented by the above general formula (I), racemizing the said acid halide by heating it to a temperature of about 80° C. to about 300° C. and then, if desired, hydrolyzing the resulting acid halide to obtain 2,2-dimethylcyclopropane-1-carboxylic acid represented by the above formula (II).

The process of the present invention will be described in more detail hereinafter.

In the racemization reaction, any of the optical isomers can be used alone or in combination in an optional proportion as the starting materials. Particularly, the residual enatiomers or antipodes after optical resolution of optically active 2,2-dimethylcyclopropane-1-carboxylic acid into one particular isomers may be advantageously utilized as the starting materials.

The 2,2-dimethylcyclopropane-1-carboxylic acid halides represented by the above general formula (I) may be obtained by the conventional methods for halogenation of the corresponding carboxylic acids, for example, by chlorination of the acid to acid chloride with thionyl chloride, sulfuryl chloride, oxalyl chloride, phosgene, phosphorus chloride, etc. or by bromination to acid bromide with a brominating agent such as phosphorus bromide. The preferred acid halides are 2,2-dimethylcyclopropane-1-carboxylic acid chloride and 2,2-dimethylcyclopropane-1-carboxylic acid bromide.

The temperature for carrying out the racemization reaction of this invention is substantially at least 80° C. The racemization speed increases with increase in the temperature, but for industrial performance the temperature is preferably not higher than about 300° C. from the viewpoint of heat stability of the acid halides.

Therefore, the reaction temperature for racemization is generally in a range of about 80° C. to about 300° C., more preferably about 100° C. to about 200° C., whereby the racemization proceeds irrespective of the reaction pressure without any trouble in the reaction.

Solvents are not especially required in the racemization reaction, but if used, it is necessary to choose such solvents which do not substantially inhibit the racemization reaction. Examples of such solvents are saturated hydrocarbons, halogenated hydrocarbons, aromatic hydrocarbons, ethers, and mixed solvents thereof.

The reaction is preferably carried out in an inert gas atmosphere such as nitrogen, argon, etc.

The reaction may be carried out in either of a batch system or a continuous system and furthermore in either of liquid phase or vapor phase.

The reaction time varies depending on heating temperature, but generally the purpose can be attained in the range of from several minutes to about 10 hours.

Progress of racemization can be determined by measuring optical rotation of a sampled reaction liquid or by reacting the sampled reaction liquid with an optically active reagent such as l-menthol to form diastereomers thereof and analyzing the mixture by gas chromatography or liquid chromatography.

The racemized 2,2-dimethylcyclopropane-1-carboxylic acid halides thus obtained can be, as (±) forms, subjected to esterification, or can be converted to the corresponding racemic carboxylic acids by hydrolyis thereof.

As explained hereinabove, the method of this invention makes it possible to convert optically active 2,2-dimethylcyclopropane-1-carboxylic acid represented by the above formula (II) into a racemic modification in an industrial scale with a high efficiency. Furthermore, it also becomes possible by combination of this method with a method of optical resolution to convert it to a more effective optically active form.

This invention will be further explained by the following Examples.

EXAMPLE 1

2.4 g of 2,2-dimethylcyclopropane-1-carboxylic acid chloride comprising 80.1% of l-form and 19.9% of d-form was charged in a glass sealed tube and heated at 135° C. for two hours. After cooling, the tube was opened to obtain the same amount of light yellow oil. A part of this product was converted to l-menthyl ester and diastereomer ratio of the ester was measured by gas chromatography to obtain 50.9% of l-form and 49.1% of d-form.

To 2.0 g of this light yellow oil was added 15.1 g of 10 wt.% aqueous sodium hydroxide solution to hydrolyze the material. The reaction mixture was extracted with methylene chloride to remove the neutral substance. Aqueous layer was acidified with an aqueous hydrochloric acid and then extracted with methylene chloride. The resulting organic layer was washed with water, dried and then concentrated to obtain 1.70 g of colorless oil. This material was distilled to obtain 1.62 g of colorless oily product having a boiling point of 85° to 87° C./10 mmHg, which had an infrared absorption spectrum corresponding with that of 2,2-dimethylcyclopropane-1-carboxylic acid.

EXAMPLE 2

10.0 g of 2,2-dimethylcyclopropane-1-carboxylic acid chloride comprising 80.1% of l-form and 19.9% of d-form was charged in a 25 ml reaction flask under nitrogen atmosphere and heated at 120° C. under stirring. During the reaction, sampling was carried out and each of the samples was converted to l-methyl ester and analyzed by gas chromatography. The results are as shown in Table 1.

TABLE 1

| Heating time (hrs) | l-form (%) | d-form (%) |
| --- | --- | --- |
| Starting material | 80.1 | 19.9 |
| 0.5 | 73.4 | 26.6 |
| 1.0 | 66.5 | 33.5 |
| 2.0 | 59.6 | 40.4 |
| 4.0 | 53.4 | 46.6 |
| 7.0 | 50.8 | 49.2 |

EXAMPLE 3

1.0 g of an ethyl acetate solution containing 10% by weight of 2,2-dimethylcyclopropane-1-carboxylic acid chloride comprising 70.3% of l-form and 29.7% of d-form was charged in a glass sealed tube and heated at 135° C. for two hours. After cooling, the tube was opened to obtain the same amount of an ethyl acetate solution. A part of this solution was converted to l-menthyl ester which had an optical isomer ratio of l-form 50.4% and d-form 49.6% measured by gas chromatography.

EXAMPLE 4

1.0 g of 2,2-dimethylcyclopropane-1-carboxylic acid chloride comprising 80.1% of l-form and 19.9% of d-form was charged in a glass sealed tube and heated at 150° C. for 30 minutes. After the reaction, the resulting product was converted to l-menthyl ester and analyzed by gas chromatography to obtain d-form 48.7% and l-form 51.3%.

EXAMPLE 5

A 50 ml reaction flask containing 5.0 g of 2,2-dimethylcyclopropane-1-carboxylic acid comprising 80.8% of d-form and 19.2% of l-form and 5.0 g of n-hexane was immersed in an oil bath at 75° C. To the mixture was added dropwise a mixed solution of 7.82 g of thionyl chloride and 2.0 g of n-hexane with stirring. After addition, the reaction mixture was stirred under heating at 75° C. for two and a half hours. After the reaction, the solvent was distilled off under a reduced pressure to obtain 5.68 g of a residual liquid having a boiling point of 58° to 60° C./55-60 mmHg. Then, the liquid was stirred for two hours under nitrogen atmosphere while heating at 135° to 140° C. in an oil bath. A part of the resulting reaction product was converted to l-menthyl ester and analyzed by gas chromatography to obtain 51.6% of d-form and 48.4% of l-form.

Then, to the reaction product was added 19.6 g of 20 wt.% aqueous solution of sodium hydroxide and a hydrolysis was carried out at 80° C. for two hours. To the reaction mixture was added 5 g of toluene and neutral matter was removed by extraction. The hydrolyzed product was acidified with aqueous hydrochloric acid and extracted with toluene. The resulting organic layer was washed with water, dried, concentrated and distilled to obtain 4.6 g of a distillate having a boiling point of 85° to 88° C./10 mmHg, which had an infrared absorption spectrum corresponding with that of racemic 2,2-dimethylcyclopropane-1-carboxylic acid.

We claim:

1. A method for racemization of an optically active 2,2-dimethylcyclopropane-1-carboxylic acid halide which comprises heating an optically active 2,2-dimethylcyclopropane-1-carboxylic acid halide represented by the general formula;

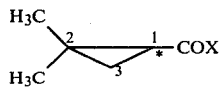

wherein X is a halogen atom to a temperature of about 80° C. to about 300° C.

2. A method for racemization of optically active 2,2-dimethylcyclopropane-1-carboxylic acid which comprises converting optically active 2,2-dimethylcyclopropane-1-carboxylic acid to a corresponding halide thereof represented by the general formula (I);

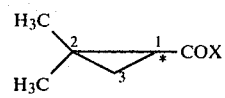

wherein X is a halogen atom, racemizing the said acid halide by heating it to a temperature of about 80° C. to about 300° C. and then hydrolyzing the resulting acid halide to obtain 2,2-dimethylcyclopropane-1-carboxylic acid represented by the general formula (II);

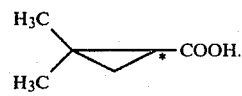

3. A method according to claim 1 wherein the heating temperature is about 100° C. to about 200° C.

4. A method according to claim 1 wherein X is chlorine or bromine atom.

5. A method according to claim 1 wherein the racemizing reaction is carried out in an inert gas atmosphere.

* * * * *